(12) United States Patent  
Baldassarre et al.

(10) Patent No.: US 8,282,966 B2  
(45) Date of Patent: **\*Oct. 9, 2012**

(54) METHODS OF REDUCING THE RISK OF OCCURRENCE OF PULMONARY EDEMA IN CHILDREN IN NEED OF TREATMENT WITH INHALED NITRIC OXIDE

(75) Inventors: James S. Baldassarre, Doylestown, PA (US); Ralf Rosskamp, Chester, NJ (US)

(73) Assignee: INO Therapeutics LLC, Hampton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/821,020

(22) Filed: Jun. 22, 2010

(65) Prior Publication Data

US 2010/0330207 A1    Dec. 30, 2010

Related U.S. Application Data

(63) Continuation of application No. 12/494,598, filed on Jun. 30, 2009, now abandoned.

(51) Int. Cl.  
*A01N 59/00* (2006.01)  
*A61K 33/00* (2006.01)  
*C01B 21/24* (2006.01)  
*A61M 16/00* (2006.01)

(52) U.S. Cl. .................. 424/718; 128/200.24; 423/405

(58) Field of Classification Search .................. None  
See application file for complete search history.

(56) References Cited

U.S. PATENT DOCUMENTS

| | | | |
|---|---|---|---|
| 5,873,359 | A | 2/1999 | Zapol et al. |
| 6,063,407 | A | 5/2000 | Zapol et al. |
| 6,601,580 | B1 | 8/2003 | Bloch et al. |
| 7,557,087 | B2 | 7/2009 | Rothbard et al. |
| 2004/0106954 | A1 | 6/2004 | Whitehurst et al. |
| 2009/0018136 | A1 | 1/2009 | Oppenheimer et al. |
| 2009/0029371 | A1 | 1/2009 | Elliott |
| 2009/0149541 | A1 | 6/2009 | Stark et al. |
| 2009/0176772 | A1 | 7/2009 | Blackburn et al. |

FOREIGN PATENT DOCUMENTS

| | | |
|---|---|---|
| EP | 1682672 A1 | 7/2006 |
| WO | WO2005004884 A2 | 1/2005 |
| WO | WO2006127907 A2 | 11/2006 |
| WO | WO2010019540 A1 | 2/2010 |

OTHER PUBLICATIONS

Beghetti et al. (Journal of Pediatrics, 1997, p. 844).*  
Macrae et al. (Intensive Care Med 2004, 30, pp. 372-380).*  
Atz et al. (Seminars in Perinatology 1997, 21(5), pp. 441-455).*  
Kinsella et al. (The Lancet 1999, 354, pp. 1061-1065).*  
The NIH (Critical Care Therapy and Respiratory Care Section; Nitric Oxide Therapy, May 2000, 13 pages).*  
Bolooki (Clinical Application of the Intra-Aortic Balloon Pump 1998, 3rd Ed. pp. 252-253).*  
Henrichsen (Journal of Pediatrics 1996, 129(1) p. 183). 2 pages.*  
(Krohn the Journal of Thoracic and Cardiovascular Surgery 1999, 117(1) pp. 195-196). 2 pages.*  
Semigran (Abstract of J Am Coll Cardiol 1994; 24: 982-988). 5 pages.*  
Hayward (Cardiovascular Research 1999; 43:628-638) 11 pages.*  
Beghetti et al. (the Journal of Pediatrics 1997 p. 844).*  
Bocchi the American Journal of Cardiology 1994, 74, pp. 70-72. 4 pages).*  
Davidson et al. (Pediatrics 1998, 101 (3) pp. 325-334).*  
The Neonatal Inhaled Nitric Oxide Study Group (The New England Journal of Medicine 1997, 336(9), pp. 597-604).*  
Macrae (Semin Neonatal 1997, 2, 49-58).*  
Miller et al. (Achives of Disease in Childhood 1994, 70, F47-F49.*  
Wheeler et al. (Pediatric Critical Care Medicine 2007, Springer, p. 278).*  
Kazerooni et al. (Cardiopulmonary Imaging 2004, Lippincott Williams & Wilkins, pp. 234-235).*  
Hurford et al. (Nitric Oxide: Biology and Pathobiology 2000 Academic Press, Chapter 56, pp. 931-945).*  
Weinberger et al. (Toxicology Sciences 2001, 59, 5-16).*  
Moss et al. (Moss and Adams' Heart Disease in Infants, Children, and Adolescents, 2007, vol. 1, p. 991 in part).*  
Bocchi et al. The American Journal of Cardiology 1994, 74, pp: 70-72. 4 pages).*  
Kazerooni et al. Cardiopulmonary Imaging 2004, Lippincott Williams & Wilkins p. 235 (2 pages).*  
"Inhaled Nitric Oxide and Hypoxic Respiratory Failure in Infants With Congenital Diaphragmatic Hernia", The Neonatal Inhaled Nitric Oxide Study Group (NINOS), Pediatrics, vol. 99, No. 6, Jun. 6, 1997, pp. 838-845.  
"Inhaled Nitric Oxide in Full-Term and Nearly Full-Term Infants with Hypoxic Respiratory Failure", The Neonatal Inhaled Nitric Oxide Study Group, N Engl J Med, 1997, vol. 336, No. 9, pp. 597-605.  
Adatia, et al, "Inhaled Nitric Oxide and Hemodynamic Evaluation of Patients With Pulmonary Hyptertension Before Transplantation", Journal of the American College of Cardiology, Elsevier, New York, NY, vol. 25, No. 7, Jun. 1, 1995, p. 1663.  
Al-Alaiyan S et al., "Inhaled nitric oxide in persistent pulmonary hypertension of the newborn refractory to high-frequency ventilation", Crit Care, vol. 3, No. 1, 1999, pp. 7-10. Argenziano, et al., "Inhaled Nitric Oxide is not a Myocardial Depressant in a Porcine Model of Heart Failure", The Journal of Thoracic and Cardiovascular Surgery, 1998, vol. 115, pp. 700-704.  
Atz AM et al., "Combined Effects of Nitric Oxide and Oxygen During Acute Pulmonary Vasodilator Testing", Journal of the American College of Cardiology (JACC), vol. 33, No. 3, Mar. 1, 1999, pp. 813-819.  
Barrington, et al., Inhaled Nitric Oxide for Preterm Infants: A Systematic Review, Pediatrics 2007; 120; 1088-1099, DOI: 10.1542/peds.2007-0726.  
Barst et al., "Nitric Oxide in Combination with Oxygen versus Either Oxygen Alone or Nitric Oxide Alone for Acute Vasodilator Testing in Children with Pulmonary Hypertemsion: A Multicenter, Randomized Study", INO Therapeutics/Ikaria, Baltimore Convention Center, May 3, 2009, 2 pages, Abstract, downloaded Jul. 2, 2009 from http://127.0.0.1:9080/PASO9A1/view.y?nu=PASO9L1_1507.  
Bland, "Pulmonary vascular dysfuction in preterm lambs with chronic lung disease", Am J Physical Lung Cell Mol Physiol 285: L76-L85, 2003.

(Continued)

*Primary Examiner* — Ernst Arnold  
(74) *Attorney, Agent, or Firm* — Fish & Richardson P.C.

(57) ABSTRACT

The invention relates methods of reducing the risk or preventing the occurrence of an adverse event (AE) or a serious adverse event (SAE) associated with a medical treatment comprising inhalation of nitric oxide.

29 Claims, No Drawings

OTHER PUBLICATIONS

Bocchi EA et al., "Inhaled Nitric Oxide Leading to Pulmonary Edema in Stable Severe Heart Failure", The American Journal of Cardiology, vol. 74, Jul. 1, 1994, pp. 70-72.

Budts W et al., "Residual pulmonary vasoreactivity to inhaled nitric oxide in patients with severe obstructive pulmonary hypertension and Eisenmenger syndrome", Heart, vol. 86, 2001, pp. 553-558.

Clark RH et al., "Low-Dose Nitric Oxide Therapy for Persistent Pulmonary Hypertension: 1-Year Follow-up", Journal of Perinatology, (2003) 23:300-303.

Clark, et al., Low-Dose Nitric Oxide Therapy for Persistent Pulmonary Hypertension: 1-Year Follow-up, Journal of Perinatology 2003; 23: 300-303.

Cockrill BA et al., "Comparison of the Effects of Nitric Oxide, Nitroprusside, and Nifedipine on Hemodynamics and Right Ventricular Contractibility in Patients With Chronic Pulmonary Hypertension", Chest, vol. 119, No. 1, Jan. 2001, pp. 128-136.

Cornfield DN et al., "Randomized, Controlled Trial of Low-dose Inhaled Nitric Oxide in the Treatment of Term and Near-term Infants With Respiratory Failure and Pulmonary Hypertension", Pediatrics, vol. 104, No. 5, pp. 1089-1094 (Nov. 5, 1999).

Cujec, et al., "Inhaled Nitric Oxide Reduction in Systolic Pulmonary Artery Pressure is Less in Patients with Decreased Left Ventricular Ejection Fraction", Canadian Journal of Cardiology, 1997, vol. 13 (9), pp. 816-824.

Davidson D et al., "Inhaled nitric oxide for the early treatment of persistent pulmonary hypertension of the term newborn: a randomized, double-masked, placebo-controlled, dose-response, multicenter study", Pediatrics, Mar. 1998; 101(3 Pt 1):325-34.

Davidson D et al., "Safety of Withdrawing Inhaled Nitric Oxide Therapy in Persistent Pulmonary Hypertension of the Newborn", Pediatrics, vol. 104, No. 2, Aug. 2, 1999, pp. 231-236.

Day RW et al., "Pulmonary Vasodilatory Effects of 12 and 60 Parts Per Million Inhaled Nitric Oxide in Children with Ventricular Septal Defect", The American Journal of Cardiology, vol. 75, Jan. 15, 1995, pp. 196-198.

Dickstein, et al., "A Theoretic Analysis of the Effect of Pulmonary Vasodilation on Pulmonary Venous Pressure: Implications for Inhaled Nitric Oxide Therapy", The Journal of Heart and Lung Transplant Jul. 1996, pp. 715-721.

Ivy, et al., "Dipyridamole attenuates rebound pulmonary hypertension after inhaled nitric oxide withdrawal in postoperative congenital heart disease", J Thorac Cardiovasc Surg 1998; 115:875-882.

Dorling, "Neurodevelopmental outcome following Nitric Oxide Therapy for Persistent Pulmonary Hypertension in Term Newborn Infants", Neonatal Intensive Care Unit, Leicester Royal Infirmary, Aug. 8, 2003, modified Nov. 12, 2003, 3 pages.

Ferguson, et al., "Inhaled nitric oxide for hypoxemic respiratory failure: Passing bad gas?", Canadian Medical Association Journal, Jan. 11, 2000; 162 (1), pp. 85-86.

Field, Neonatal Ventilation With Inhaled Nitric Oxide Versus Ventilatory Support Without Inhaled Nitric Oxide for Preterm Infants With Severe Respiratory Failure: The INNOVO Multicentre Radomised Controlled Trial (ISRCTN 17821339), "Pediatrics" Journal 2005:115:926-936, DOI: 10.1542/peds.2004-1209.

Findlay, "Paradoxical Haemodynamic Response to Inhaled Nitric Oxide", International Journal of Intensive Care 1998 GB, vol. 5, No. 4, 1998, pp. 134-139.

Finer NN et al., "Randomized, Prospective Study of Low-Dose Versus High-Dose Inhaled Nitric Oxide in the Neonate With Hypoxic Respiratory Failure", Pediatrics, vol. 108, No. 4, Oct. 4, 2001.

Greenough, "Inhaled nitric oxide in the neonatal period", Expert Opinion on Investigational Drugs, 2000 Ashley Publications Ltd, 1354-3784, 9 pages.

Hayward CS et al., "Effect of Inhaled Nitric Oxide on Normal Human Left Ventricular Function," JACC, vol. 30, No. 1, Jul. 1997, pp. 49-56.

Hayward CS et al., "Inhaled Nitric Oxide in Cardiac Failure: Vascular Versus Ventricular Effects", Journal of Cardiovascular Pharmacology, vol. 27, 1996, pp. 80-85, Abstract Only.

Hayward et al., "Left Ventricular Chamber Function During Inhaled Nitric Oxide in Patients with Dilated Cardiomyopathy", J. Cardiovascular Pharmacology, vol. 34, Iss. 5, Nov. 1999, pp. 749-754, Abstract.

Henrichsen, et al., "Inhaled Oxide Can Cause Severe Systemic Hypotension", Journal of Pediatrics, Mosby-Year Book, St. Louis, MO, vol. 129, No. 1, Jul. 1996, p. 183.

Inglessis I et al., "Does inhaled nitric oxide support the hemodynamic of spontaneous breathing patients with cardiogenic shock related to right ventricular myocardial infarction? Reply", JACC, vol. 45, No. 6, Mar. 15, 2005, pp. 965-966.

Inglessis I et al., "Hemodynamic effects of inhaled nitric oxide in right ventricular myocardial infarction and cardiogenic shock", JACC, vol. 44, No. 4, Aug. 18, 2004, pp. 793-798.

"Inhaled Nitric Oxide (INO) in Hypoxic Respiratory Failure", Study description, study sponsored by INO Therapeutics, ClinicalTrials. gov Identifier NCT00922532, Jun. 16, 2009, 4 pages.

Krasuski RA et al., "Inhaled Nitric Oxide Selectively Dilates Pulmonary Vasculature in Adult Patients With Pulmonary Hypertension, Irrespective of Etiology", Journal of the American College of Cardiology (JACC), vol. 36, No. 7, Dec. 2000, pp. 2204-2211.

Lipshultz, "Ventricular dysfunction clinical research in infants, children and adolescents", Progress in Pediatric Cardiology 12 (2000) 1-28.

Loh, et al., "Cardiovascular Effects of Inhaled Nitric Oxide in Patients with Left Ventricular Dsyfunction," Circulation, Aug. 7, 1994, 90, pp. 2780-2785.

Magee et al., "Comparison of Supplemental Oxygen and Nitric Oxide for Inhalation plus oxygen in the evaluation of the reactivity of the pulmonary vasculature during Acute Pulmonary Vasodilator Testing", Oct. 1-31, 2006, Reserach project description, 1 page, http://www.rbht.nhs.uldresearch.

Matsumoto A et al., "Effect of Inhaled Nitric Oxide on Gas Exchange in Patients with Congestive Heart Failure", Annals of Internal Medicine, vol. 130, No. 1, 1999:40-44.

Morales-Blanhir J et al., "Clinical value of vasodilator test with inhaled nitric oxide for predicting long-term response to oral vasodilators in pulmonary hypertension", Respiratory Medicine, vol. 98, 2004, pp. 225-234.

Murray, et al., "Nitric Oxide and Septic Vascular Dysfunction", Anesth Analg 2000; 90:89-101.

Natori S et al., "Inhaled Nitric Oxide Modifies Left Ventricular Diastolic Stress in the Presence of Vasoactive Agents in Heart Failure", Am J Respir Crit Care Med, vol. 167, pp. 895-901, 2003.

Ovodov, et al., "Nitric Oxide: Clinical Applications", Seminars in Aneshesia, Saunders, CO, New York NY, vol. 19, No. 2, Jun. 1, 2000, pp. 88-97.

Pepke-Zaba J et al., "Inhaled nitric oxide as a cause of selective pulmonary vasodilation in pulmonary hypertension", The Lancet, vol. 338, Nov. 9, 1991, pp. 1173-1174.

Ricciardi MJ et al., Inhaled Nitric Oxide in Primary Pulmonary Hypertension: A Safe and Effective Agent for Predicting Response to Nifedipine, Journal of the American College of Cardiology (JACC,) vol. 32, No. 4, Oct. 1998, pp. 1068-1073.

Roberts, Inhaled Nitric Oxide and Persistent Pulmonary Hypertension of the Newborn, The New England Journal of Medicine, Feb. 27, 1997, vol. 336, No. 9, pp. 605-610.

Rosales, et al., "Hemodynamic Effects Observed with Inhaled Nitric Oxide After Surgical Repair of Total Anamolous Pulmonary Venous Return", Pediatric Cardiology, 1999, vol. 20, pp. 224-226.

Sadiq HF et al., "Inhaled Nitric Oxide in the Treatment of Moderate Persistent Pulmonary Hypertension of the Newborn: A Randomized Controlled, Multicenter Trial", Journal of Perinatology, 2003; 23:98-103.

Sehgal A et al., "Experience with Inhaled Nitric Oxide Therapy in Hypoxic Respiratory Failure of the Newborn", Indian J Chest Dis Allied Sci, 2005; 47:245-49.

Semigran et al., "Hemodynamic Effects of Inhaled Nitric Oxide in Heart Failure", Journal of American College of Cardiology (JACC), vol. 24, No. 4, Oct. 1994, pp. 982-988.

Singh, et al., "Nitric Oxide, the biological mediator of the decade: fact of fiction?", Eur Respir J 1997; 10: 699-707.

Smyth RL, "Inhaled nitric oxide treatment for preterm infants with hypoxic respiratory failure", Thorax, 2000;55(Suppl 1):S51-S55.

Steinhorn, RH, "Pulmonary Hypertension, Persistent-Newborn", Updated Apr. 19, 2007, http://emedicine.medscape.com/article/898437-overview.

Steinhorn, et al., "Inhaled nitric oxide enhances oxygenation but not survival in infants with alveolar capillary dysplasia", The Journal of Pediatrics, Mar. 1997, pp. 417-422.

"Use of Inhaled Nitric Oxide", American Academy of Pediatrics—Committee on Fetus and Newborn, Pediatrics vol. 106, No. 2, Aug. 2000, pp. 344-345.

Watson, et al., "Clinical and Economic Effects of iNO in Premature Newborns With Respiratory Failure at 1 Year", Pediatrics 2009; 124; 1333-1343.

Weinberger B et al., "The Toxicology of Inhaled Nitric Oxide", Toxicological Sciences, 59, pp. 5-16 (2001).

Weinberger, et al., "Nitric Oxide in the lung: therapeutic and cellular mechanisms of action", Pharmacology & Therapeutics 84 (1999) 401-411.

Wessel DL et al., "Improved Oxygenation in a Randomized Trial of Inhaled Nitric Oxide for Persistent Pulmonary Hypertension of the Newborn", Pediatrics, vol. 100, No. 5, Nov. 5, 1997.

AU 2009202685 Office Action dated Jun. 17, 2010 (3 pages).

AU 2009202685 Office Action Response dated Jul. 29, 2010, 19 pages.

Branson, Inhaled Nitric Oxide in Adults, The Science Journal of the American Association for Respiratory Care 1997 Open Forum Abstracts, Dec. 7, 1997, 2 pages, retrieved at <<http://www.rcjournal.com/abstracts/1997/?id=A00000929>> on Dec. 22, 2010.

Braunwald, Heart Failure, chapter 233 of Harrison's Principles of Internal Medicine, 14th Edition, 1998, pp. 1287-1291 & 1360.

Clark, et al., Low-Dose Nitric Oxide Therapy for Persistent Pulmonary Hypertension of the Newborn, New England Journal of Medicine, vol. 342, No. 7, pp. 469-474.

"Comparison of Supplemental Oxygen and Nitric Oxide for Inhalation in the Evaluation of the Reactivity of the Pulmonary Vasculature During Acute Pulmonary Vasodilator Testing," ClinicalTrials.gov archive, updated Jan. 12, 2009, 4 pages, retrieved at <<http://clinicaltrials.gov/archive/NCT00626028/2009_01_12 Jan. 12, 2009>>.

Cox, et al., Factors Associated With Establishing a Causal Diagnosis for Chidren With Cardiology, Pediatrics, vol. 118, No. 4, Oct. 4, 2006, pp. 1519-1531, published online Oct. 2, 2006.

Cuthbertson et al., "UK guidelines for the use of inhaled nitric oxide therapy in adults ICUs*", Intensive Care Med (1997), 23, Springer-Verlag, 1997, pp. 1212-1218.

Dorland, "The American Illustrated Medical Dictionary", 7th Edition, W.B. Saunders Company, 1914, pp. 113.

EP 09251949 Office Action dated Oct. 11, 2010, 5 pages.

Guideline for Industry; Clinical Safety Data Management: Definitions and Standards for Expedited Reporting, Mar. 1995, 17 pages.

Headrick, Hemodynamic monitoring of the critically ill neonate, J Perinat Neonatal Nurs 1992; 5(4): 58-67.

INO Therapeutics, LLC, "INOflo for Inhalation 800ppm", package leaflet, 2010, 2.

JP 2009157623 Office Action dated Feb. 23, 2010, 3 pages.

JP 2009157623 Office Action dated Jul. 30, 2010, 6 pages.

JP 2009157623 Office Action response filed Jun. 18, 2010, 37 pages (no translation).

JP 2009157623 request for accelerated exam filed Jan. 15, 2010 (60 pages).

JP 2009157623 response filed Nov. 30, 2010, 58 pages.

Letter of Acceptance for AU 2010202422, dated Oct. 7, 2010.

Letter of acceptance of AU application 2009202685, dated Aug. 10, 2010, 3 pages.

Lipschultz, The incidence of pediatric cardiomyopathy in two regions of the United States, New England Journal of Medicine, Apr. 24, 2003. <<http://www.nejm.org/doi/full/10.1056/NEJMoa021715>>.

NIH Clinical Center Services, retrieved at <http://www.cc.nih.gov/ccmd/clinical_services.html>> on Aug. 18, 2010.

Office Action for AU 2010202422 dated Jul. 9, 2010, 3 pages.

Office Action from AU 2009202685 dtd Mar. 15, 2010.

Office Action from AU 2010206032 dated Aug. 16, 2010 (3 pages).

Office Action Response for AU 2009202685 to Mar. 15, 2010 OA, filed Jun. 8, 2010 (16 pages).

Office Action Response for JP2007157623 filed on Nov. 12, 2009 (no English translation).

Office Action Response to AU 2010202422 OA dated Jul. 9, 2010, response filed Sep. 1, 2010.

PCT/US2010/038652 Search Report dated Jul. 29, 2010, 16 pages.

Response filed Aug. 18, 2010 to EP Search Report dated May 10, 2010 for EP09251949.

Search Report from EP 09251949 dated May 10, 2010.

Towbin, et al., Incidence, Causes, and Outcomes of Dilated Cardiomyopathy in Children, JAMA, Oct. 18, 2006—vol. 296, No. 15, pp. 1867-1876.

Yoshida, Kiyoshi, "Well-illustrated Diagnostics and Treatment of Heart Failure" Professor of Kawasaki Medical University, cardiovascular internal medicine Circulation Up-to-Date vol. 2, No. 4, 2007(343), pp. 23-28.

Behera, et al., Nesiritide Improves Hemodynamics in Children with Dilated Cardiomyopathy: A Pilot Study, Pediatr Cardiol (2009) 30:26-34.

Bhagavan, et al., Potential role of ubiquinone (coenzyme Q10) in pediatric cardiomyopathy, Clinical Nutrition (2005) 24, 331-338, pp. 331-338.

Bublik, et al., Pediatric cardiomyopathy as a chronic disease: A perspective on comprehensive care programs, Progress in Pediatric Cardiology 25 (2008) 103-111.

Cox, et al., Factors Associated with Establishing a Causal Diagnosis for Children with Cardiomyopathy, Pediatrics vol. 118, No. 4, Oct. 2006, pp. 1519-1531.

Dermatological Cryosurgery in Primary Care with Dimethyl Ether Propane Spray in Comparison with Liquid Nitrogen, Martinez, et al., Atnecion Primaria, vol. 18, No. 5, (211, 216), Sep. 30, 1996.

Dronedarone is Less Effective, But Safer Than Amiodarone in Atrial Fibrillation, Oct. 27, 2009, p. 3, <<http://www.npci.org.uk/blog/?p=778>>.

Early Inhaled Nitric Oxide Therapy in Term and Near Term Infants with Respiratory Failure, from ClinicalTrials.gov archive, NCT00005773, Jun. 23, 2005.

Ehrenkranz RA, "Inhaled Nitric Oxide in Full-Term and Nearly Full-Term Infants with Hypoxic Respiratory Failure", The Neonatal Inhaled Nitric Oxide Study Group, N Engl J Med, 1997, vol. 336, No. 9, pp. 597-605.

Elbl, et al., Long-term serial echocardiographic examination of late anthracycline cardiotoxicity and its prevention by dexrazoxane in paediatric patients, Eur J Pediatr (2005) 164: 678-684.

The Encarta Webster's Dictionary of the English Language (2004) is the second edition of the Encarta World Dictionary, published 1999, <<http://encarta.msn.com/encnet/features/dictionary/dictionaryhome.aspx>>; used to look up the definitions of "precaution" and "exclusion".

Green, "Patent Ductus Ateriosus Demonstrating Shunting of Blood", Figure from presentation given Jan. 10, 2011, pp. 1.

Harrison's Principles of Internal Medicine, Fauci, et al., p. 1287-1291 and 1360, 12th edition, McGraw Hill, 1998.

Huddleston, Indications for heart transplantation in children, Progress in Pediatric Cardiology 26 (2009) 3-9.

Inhaled Nitric Oxide by Oxygen Hood in Neonates, from ClinicalTrials.gov, NCT00732537, Aug. 8, 2008.

Inhaled Nitric Oxide in Neonates with Elevated A-a DO2 Gradients Not Requiring Mechanical Ventilation, from ClinicalTrials.gov archive, NCT00041548, Jun. 23, 2005, 2 pages.

James, et al., Treatment of heart failure in children, Current Paediatrics (2005) 15, 539-548.

JP 2009-157623 Office Action dated Feb. 15, 2011, 3 pages.

Lavigne, et al., Cardiovascular Outcomes of Pediatric Seroreverters Perinatally Exposed to HAART, Cardiovascular Toxicology (2004) 04 187-197.

Lipschultz, The effect of dexrazoxane on myocardial injury in doxorubicin-treated children with acute lymphoblastic leukemia, New England Journal of Medicine 2004; 351:145-153.

Lipshultz, et al., Cardiovascular status of infants and children of women infected with HIV-1 (P2C2 HIV): a cohort study, The Lancet, vol. 360, Aug. 3, 2002, pp. 368-373.

Lipshultz, et al., Cardiovascular Trials in Long-Term Survivors of Childhood Cancer, Journal of Clinical Oncology, vol. 22, No. 5, Mar. 1, 2004, pp. 769-773.

Lipshultz, Chronic Progressive Cardiac Dysfuction Years After Doxorubicin Therapy for Childhood Acute Lymphoblastic Leukemia, Journal of Clinical Oncology, vol. 23, No. 12, Apr. 20, 2005. 8 pages.

Lipshultz, Clinical research directions in pediatric cardiology, Current Opinion in Pediatrics 2009, 21:585-593.

Lipshultz, Establishing norms for echocardiographic measurement of cardiovascular structures and function in children, J Appl Physiol 99: 386-388, 2005.

Lipshultz, Frequency of clinically unsuspected myocardial injury at a children's hospital, American Heart Journal, vol. 151, No. 4, pp. 916-922.

Lipshultz, et al., Long-Term Enalapril Therapy for Left Ventricular Dysfunction in Doxorubicin-Treated Survivors of Childhood Cancer, Journal of Clinical Oncology, vol. 20, No. 23 Dec. 1, 2002; pp. 4517-4522.

Madriago, Heart Failure in Infants and Children, Pediatrics in Review, 2010; 31:4-12.

Miller, et al., Nutrition in Pediatric Cardiomyopathy, Prog Pediatr Cardiol, Nov. 2007; 24(1): 59-71.

Mone, Effects of Environmental Exposures on the Cardiovascular System: Prenatal Period Through Adolescence, Pediatrics vol. 113, No. 4, Apr. 2004, pp. 1058-1069.

NIH Clinical Center, Department Policy and Procedure Manual for the Critical Care Therapy and Respiratory Care Section; Nitric Oxide Therapy, 2000, sections 3.1-3.1.2 & 5.2.3.

Notification of Reason for Rejection, mailed Jul. 30, 2010, from Japanese Patent Application No. 2009-157623.

Japanese Office Action mailed Feb. 15, 2011 for Japanese Patent Application No. 2009-157623, a counterpart foreign application for U.S. Appl. No. 12/494,598.

Pazopanib Plus Lapatinib Compared to Lapatinib Alone in Subjects With Inflammatory Breast Cancer, Apr. 22, 2010, p. 4, ClinicalTrials.gov, <<http://clinicaltrials.gov/ct2/show/NCT00558103>>.

Ratnasamy, et al., Associations between neurohormonal and inflammatory activation and heart failure in children, American Heart Journal, Mar. 2008, pp. 527-533.

NIY Clinical Center 2 Critical Care Medicine Department Sample Rotations, Updated Jan. 2007.

Sibutramine-metformin Combination vs. Sibutramine and Metformin Monotherapy in Obese Patients, Jul. 15, 2009, p. 3, ClinicalTrials.gov, <<http://clinicaltrials.gov/ct2/showNCT00941382>>.

Somarriba, et al., Exercise rehabilitation in pediatric cardiomyopathy, Progress in Pediatric Cardiology 25 (2008) 91-102.

Steinhorn, Pulmonary Hypertension, Persistent-Newborn, from emedicine from WebMD, article last updated on Apr. 19, 2007, 15 pages.

Strauss, et al., Pediatric Cardiomyopathy—A Long Way to Go, The New England Journal of Medicine, 348; 17, Apr. 24, 2003, pp. 1703-1705.

Study of Comparative Effects of Oral Clonidine vs. Oral Diazepam Pre-Medication on the Extent and Duration of Sensory Blockade in Patients Undergoing Vaginal Hysterectomy Under Spinal Anaesthesia, Toshniwal, et al., Interenet Journal of Anesthesiology, 2009, <<http://www.britannica.com/bps/additionalcontent/18/41575551/Study-of-Comparative-Effects-Oral-Clonidine-vs-Oral-Diazepam-Pre-Medication-on-the-Extent-and-Duration-of-Sensory-Blockade-in-Patients-Undergoing-Vaginal-Hysterectomy-Under-Spinal-Anaesthesia>>.

The Effects of Nitric Oxide for Inhalation on the Development of Chronic Lung Disease in Pre-Term Infants, from ClinicalTrials.gov archive, NCT00551642, Oct. 30, 2007, 3 pages.

van Dalen, Treatment for Asymptomatic Anthracycline-Induced Cardiac Dysfunction in Childhood Cancer Survivors: The Need for Evidence, Journal of Clinical Oncology, vol. 21, No. 17, Sep. 11, 2003, pp. 3375-3379.

Wilkinson, et al., Epidemiological and outcomes research in children with pediatric cardiomyopathy; discussions from the international workshop on primary and idiopathic cardiomyopathies in children, Progress in Pediatric Cardiology 25 (2008) 23-25.

Azeka, et al., "Effects of Low Doses of Inhaled Nitric Oxide Combined with Oxygen for the Evaluation of Pulmonary Vascular Reactivity in Patients with Pulmonary Hypertension," Pediatric Cardiol, vol. 23, pp. 20-26 (2002).

Barst et al., "Vasodilator Testing with Nitric Oxide and/or Oxygen in Pediatric Pulmonary Hypertension," Pediatr. Cardiol., vol. 31, pp. 598-606 (2010).

Beghetti et al., "Inhaled nitric oxide and congenital cardiac disease," Cardiol. Young, vol. 11, pp. 142-152 (2001).

Bichel et al., "Successful weaning from cardiopulmonary bypass after cardiac surgery using inhaled nitric oxide," Pediatric Anaesthesia, vol. 7, pp. 335-339 (1997).

Bin-Nun et al., "Role of iNO in the modulation of pulmonary vascular resistance," Journal of Perinatology, vol. 28, pp. S84-S92 (2008).

Dickstein et al., "A theoretic analysis of the effect of pulmonary vasodilation on pulmonary venous pressure: Implications for inhaled nitric oxide therapy," J Heart Lung Transplant, vol. 15, pp. 715-721 (1996).

Haddad et al., "Use of inhaled nitric oxide perioperatively and in intensive care patients," Anesthesiology, vol. 92, pp. 1821-1825 (2000).

Hare et al., "Influence of Inhaled Nitric Oxide on Systemic Flow and Ventricular Filling Pressure in Patients Receiving Mechanical Circulatory Assistance," Circulation, vol. 95, pp. 2250-2253 (1997).

Hayward et al., "Inhaled Nitric Oxide in Cardiac Failure: Vascular Versus Ventricular Effects," Journal of Cardiovascular Pharmacology, vol. 27, pp. 80-85 (1996).

Kieler-Jensen et al., "Inhaled nitric oxide in the evaluation of heart transplant candidates with elevated pulmonary vascular resistance," J Heart Lung Transplant, vol. 13, pp. 366-375 (1994).

Kulik, "Inhaled nitric oxide in the management of congenital heart disease," Current Opinion in Cardiology, vol. 11, pp. 75-80 (1996).

Madriago et al., "Heart Failure in Infants and Children," Pediatrics in Review, vol. 31, pp. 4-12 (2010).

Semigran et al., "Hemodynamic effects of inhaled nitric oxide in heart failure," J Am Col Cardiol, vol. 24, pp. 982-988 (1994).

Steudel et al., "Inhaled nitric oxide," Anesthesiology, vol. 91, pp. 1090-1121 (1999).

Wessel et al., "Managing low cardiac output syndrome after congenital heart surgery," Crit. Care Med., vol. 29(10) pp. S220-S230 (2001).

Office Action in U.S. Appl. No. 12/821,041, mailed Feb. 10, 2012, 34 pages.

Fish & Richardson P.C., Supplemental Amendment and Remarks in U.S. Appl. No. 12/821,041, filed May 11, 2012 (32 pages).

European Patent Office minutes of oral proceedings in EP 09 251 949.5, with allowable claims (7 pages), dated May, 23, 2012.

Barst et al., "Vasodilator Testing with Nitric Oxide and/or Oxygen in Pediatric Pulmonary Hypertension," Received: Sep. 14, 2009 / Accepted: Jan. 19, 2010 Springer Science + Business Media, LLC, 2010, 9 pages.

Beggs et al., "Cardiac Failure in Children," 17th Expert Committee on the Selection and Use of Essential Medicines, Geneva, Mar. 2009, 31 pages.

Canadian Office Action mailed May 31, 2011 for Canadian patent application No. 2671029, a counterpart foreign application of U.S. Appl. No. 12/494,598.

UTMB Respiratory Care Services, "Delivery of Inhaled Nitric Oxide Therapy through an Adult or Pediatric Nasal Cannula," (4 pages) Jul. 2003.

Douwes et al., "The Maze of Vasodilator Response Criteria," Published online: Nov. 26, 2010, Pediatr Cardiol, (2011) 32: pp. 245-246.

Fraisse et al., "Acute pulmonary hypertension in infants and children: cGMP-related drugs," Pediatric Crit Care Med 2010, vol. 11, No. 2 (Suppl.), 4 pages.

Fraisse et al., "Doppler echocardiographic predictors of outcome in newborns with persistent pulmonary hypertension," Cardiol. Young, vol. 14, pp. 277-283, 2004.

Ichinose et al., "Inhaled Nitric Oxide, A Selective Pulmonary Vasodilator: Current Uses and Therapeutic Potential," Circulation, vol. 109, pp. 3106-3111, Feb. 11, 2011.

INOmax (nitric oxide) for inhalation 100 and 800 ppm (parts per million), drug label insert, 2007, 2 pages.

Kay et al., "Congestive heart failure in pediatric patients," From the Department of Pediatrics, Duke University Medical Center, 2001, by Mosby, Inc., 6 pages.

Konduri et al., "A Randomized Trial of Early Versus Standard Inhaled Nitric Oxide Therapy in Term and Near-Term Newborn Infants With Hypoxic Respiratory Failure," Pediatrics, vol. 113, pp. 559-564, 2004.

Malloy, "Nitric Oxide Weaning, RT: for Decision Makers in Respiratory Care," http://rtmagazine.com/issues/articles/2000-12_05.asp, 3 pages, Dec. 2000.

Rosenberg, "Inhaled nitric oxide in the premature infant with severe hypoxemic respiratory failure: A time for caution," The Journal of Pediatrics, vol. 133, pp. 720-722, Dec. 1998.

Advances in Pulmonary Hypertension, vol. 7(4), pp. 1-418, Winter 2008-2009 (entire issue).

Non-final Office Action in U.S. Appl. No. 12/820,866, mailed Jun. 8, 2011, 33 pages.

Lee & Hayes, Amendment in Reply to Office Action in U.S. Appl. No. 12/820,866, mailed Jun. 8, 2011, filed Jul. 8, 2011, 105 pages.

Final Office Action in U.S. Appl. No. 12/820,866, mailed Aug. 24, 2011, 27 pages.

Fish & Richardson P.C., Brief on Appeal in U.S. Appl. No. 12/820,866, filed Oct. 4, 2011, 211 pages.

Examiner Answer in U.S. Appl. No. 12/820,866, mailed Nov. 1, 2011, 27 pages.

Fish & Richardson P.C., Reply Brief in U.S. Appl. No. 12/820,866, filed Dec. 16, 2011, 21 pages.

Fish & Richardson P.C., Supplement to the Reply Brief in U.S. Appl. No. 12/820,866, filed Jan. 3, 2012, 3 pages.

Non-Final Office Action for U.S. Appl. No. 12/820,980, mailed Jun. 10, 2011, 30 pages.

Lee & Hayes, Amendment in Reply to Office Action in U.S. Appl. No. 12/820,980, mailed Jun. 10, 2011, filed Jul. 11, 2011, 99 pages.

Final Office Action in U.S. Appl. No. 12/820,980, mailed Sep. 9, 2011, 26 pages.

Non final Office Action in U.S. Appl. No. 12/821,041, mailed Aug. 17, 2010, 24 pages.

Lee & Hayes, Reply Amendment in U.S. Appl. No. 12/821,041, mailed Aug. 17, 2010, filed Feb. 14, 2011, 28 pages.

Final Office Action in U.S. Appl. No. 12/821,041, mailed Jun. 27, 2011, 36 pages.

Fish & Richardson P.C., Amendment in Reply to Office Action in U.S. Appl. No. 12/821,041, mailed Jun. 27, 2011, filed Jan. 6, 2012, 155 pages.

Bates, "Inhaled Nitric Oxide: A Selective Pulmonary Vasodilator," 2004, 9 pages.

Definition of "Contraindication" on Medicine.net.com; http://www.medterms.com/script/main/art.asp?articlekey=17824; retrieved Mar. 14, 2011; 2 pages.

Murray et al., "Angiotensin Converting Enzyme Inhibitory Peptides Derived from Food Proteins: Biochemistry, Bioactivity and Production," Current Pharmaceutical Design, 2007, pp. 773-791.

NIH CC: Critical Care Services, http://www.cc.nih.gov/ccmd/clinical_services.html; retrieved Mar. 10, 2011, 3 pages.

Guidelines for Industry: Clinical Safety Data Management<<www.fda.gov/downloads/Drugs/GuidanceComplianceRegulatoryInformation/Guidance/ucm073087.pdf>>, Mar. 1995, 17 pages.

UCI General Clinical Research Center, <<http://www.gcrc.uci.edu/rsa/aer.cfm>>, retrieved Sep. 13, 2010, 2 pages.

INO Therapeutics, "Comparison of Inhaled Nitric Oxide and Oxygen in Patient Reactivity during Acute Pulmonary Vasodilator Testing," downloaded from clinicaltrials.gov on Apr. 23, 2012; first received on Feb. 20, 2008; last updated on Oct. 18, 2010.

* cited by examiner

METHODS OF REDUCING THE RISK OF OCCURRENCE OF PULMONARY EDEMA IN CHILDREN IN NEED OF TREATMENT WITH INHALED NITRIC OXIDE

CROSS REFERENCE TO RELATED APPLICATIONS

This application claims priority to U.S. patent application Ser. No. 12/494,598, entitled "Methods of Treating Term and Near-Term Neonates Having Hypoxic Respiratory Failure Associated with Clinical or Echocardiographic Evidence of Pulmonary Hypertension", filed on Jun. 30, 2009, incorporated herein by reference.

BACKGROUND OF THE INVENTION

INOmax®, (nitric oxide) for inhalation is an approved drug product for the treatment of term and near-term (>34 weeks gestation) neonates having hypoxic respiratory failure associated with clinical or echocardiographic evidence of pulmonary hypertension.

The use of inhaled NO (iNO) has been studied and reported in the literature. (Kieler-Jensen M et al., 1994, Inhaled Nitric Oxide in the Evaluation of Heart Transplant Candidates with Elevated Pulmonary Vascular Resistance, *J Heart Lung Transplantation* 13:366-375; Pearl R G et al., 1983, Acute Hemodynamic Effects of Nitroglycerin in Pulmonary Hypertension, *American College of Physicians* 99:9-13; Ajami G H et al., 2007, Comparison of the Effectiveness of Oral Sildenafil Versus Oxygen Administration as a Test for Feasibility of Operation for Patients with Secondary Pulmonary Arterial Hypertension, *Pediatr Cardiol*; Schulze-Neick I et al., 2003, Intravenous Sildenafil Is a Potent Pulmonary Vasodilator in Children With Congenital Heart Disease, *Circulation* 108 (Suppl II):II-167-II-173; Lepore J J et al., 2002, Effect of Sildenafil on the Acute Pulmonary Vasodilator Response to Inhaled Nitric Oxide in Adults with Primary Pulmonary Hypertension, *The American Journal of Cardiology* 90:677-680; and Ziegler J W et al., 1998, Effects of Dipyridamole and Inhaled Nitric Oxide in Pediatric Patients with Pulmonary Hypertension, *American Journal of Respiratory and Critical Care Medicine* 158:1388-95).

SUMMARY OF THE INVENTION

One aspect of the invention relates to a pre-screening methodology or protocol having exclusionary criteria to be evaluated by a medical provider prior to treatment of a patient with iNO. One objective of the invention is to evaluate and possibly exclude from treatment patients eligible for treatment with iNO, who have pre-existing left ventricular dysfunction (LVD). Patients who have pre-existing LVD may experience, and are at risk of, an increased rate of adverse events or serious adverse events (e.g., pulmonary edema) when treated with iNO. Such patients may be characterized as having a pulmonary capillary wedge pressure (PCWP) greater than 20 mm Hg, and should be evaluated on a case-by-case basis with respect to the benefit versus risk of using iNO as a treatment option.

Accordingly, one aspect of the invention includes a method of reducing the risk or preventing the occurrence, in a human patient, of an adverse event (AE) or a serious adverse event (SAE) associated with a medical treatment comprising inhalation of nitric oxide, said method comprising the steps or acts of (a) providing pharmaceutically acceptable nitric oxide gas to a medical provider; and, (b) informing the medical provider that excluding human patients who have pre-existing left ventricular dysfunction from said treatment reduces the risk or prevents the occurrence of the adverse event or the serious adverse event associated with said medical treatment.

Further provided herein is a method of reducing the risk or preventing the occurrence, in a human patient, of an adverse event or a serious adverse event associated with a medical treatment comprising inhalation of nitric oxide, said method comprising the steps or acts of (a.) providing pharmaceutically acceptable nitric oxide gas to a medical provider; and, (b.) informing the medical provider that human patients having pre-existing left ventricular dysfunction experience an increased risk of serious adverse events associated with said medical treatment.

Another aspect of the invention is a method of reducing one or more of an AE or a SAE in an intended patient population in need of being treated with iNO comprising the steps or acts of (a.) identifying a patient eligible for iNO treatment; (b) evaluating and screening the patient to identify if the patient has pre-existing LVD, and (c) excluding from iNO treatment a patient identified as having pre-existing LVD.

Another aspect of the invention is a method of reducing the risk or preventing the occurrence, in a patient, of one or more of an AE or a SAE associated with a medical treatment comprising iNO, the method comprising the steps or acts of (a.) identifying a patient in need of receiving iNO treatment; (b.) evaluating and screening the patient to identify if the patient has pre-existing LVD; and (c.) administering iNO if the patient does not have pre-existing LVD, thereby reducing the risk or preventing the occurrence of the AE or the SAE associated with the iNO treatment. Alternatively, step (c) may comprise further evaluating the risk versus benefit of utilizing iNO in a patient where the patients has clinically significant LVD before administering iNO to the patient.

In an exemplary embodiment of the method, the method further comprises informing the medical provider that there is a risk associated with using inhaled nitric oxides in human patients who have preexisting or clinically significant left ventricular dysfunction and that such risk should be evaluated on a case by case basis.

In another exemplary embodiment of the method, the method further comprises informing the medical provider that there is a risk associated with using inhaled nitric oxide in human patients who have left ventricular dysfunction.

In an exemplary embodiment of the methods described herein, a patient having pre-existing LVD is characterized as having PCWP greater than 20 mm Hg.

In an exemplary embodiment of the method, the patients having pre-existing LVD demonstrate a PCWP≧20 mm Hg.

In another exemplary embodiment of the method, the iNO treatment further comprises inhalation of oxygen ($O_2$) or concurrent ventilation.

In another exemplary embodiment of the method, the patients having pre-existing LVD have one or more of diastolic dysfunction, hypertensive cardiomyopathy, systolic dysfunction, ischemic cardiomyopathy, viral cardiomyopathy, idiopathic cardiomyopathy, autoimmune disease related cardiomyopathy, drug-related cardiomyopathy, toxin-related cardiomyopathy, structural heart disease, valvular heart disease, congenital heart disease, or, associations thereof.

In another exemplary embodiment of the method, the patient population comprises children.

In another exemplary embodiment of the method, the patient population comprises adults.

In another exemplary embodiment of the method, the patients who have pre-existing LVD are at risk of experiencing and increased rate of one or more AEs or SAEs selected from pulmonary edema, hypotension, cardiac arrest, electrocardiogram changes, hypoxemia, hypoxia, bradycardia or associations thereof.

In another exemplary embodiment of the method, the intended patient population in need of being treated with inhalation of nitric oxide has one or more of idiopathic pulmonary arterial hypertension characterized by a mean pulmonary artery pressure (PAPm)>25 mm Hg at rest, PCWP≦15 mm Hg, and, a pulmonary vascular resistance index (PVRI)> 3 u·m$^2$; congenital heart disease with pulmonary hypertension repaired and unrepaired characterized by PAPm>25 mm Hg at rest and PVRI>3 u·m$^2$; cardiomyopathy characterized by PAPm>25 mm Hg at rest and PVRI>3 u·m$^2$; or, the patient is scheduled to undergo right heart catheterization to assess pulmonary vasoreactivity by acute pulmonary vasodilatation testing.

In another exemplary embodiment of any of the above methods, the method further comprises reducing left ventricular afterload to minimize or reduce the risk of the occurrence of an adverse event or serious adverse event being pulmonary edema in the patient. The left ventricular afterload may be minimized or reduced by administering a pharmaceutical dosage form comprising nitroglycerin or calcium channel blocker to the patient. The left ventricular afterload may also be minimized or reduced using an intra-aortic balloon pump.

DETAILED DESCRIPTION OF THE EXEMPLARY EMBODIMENTS

INOmax® (nitric oxide) for inhalation was approved for sale in the United States by the U.S. Food and Drug Administration ("FDA") in 1999. Nitric oxide, the active substance in INOmax®, is a selective pulmonary vasodilator that increases the partial pressure of arterial oxygen (PaO2) by dilating pulmonary vessels in better ventilated areas of the lung, redistributing pulmonary blood flow away from the lung regions with low ventilation/perfusion (V/Q) ratios toward regions with normal ratios. INOmax® significantly improves oxygenation, reduces the need for extracorporeal oxygenation and is indicated to be used in conjunction with ventilatory support and other appropriate agents. The current FDA-approved prescribing information for INOmax® is incorporated herein by reference in its entirety. The CONTRAINDICATIONS section of the prescribing information for INOmax® states that INOmax® should not be used in the treatment of neonates known to be dependent on right-to-left shunting of blood.

INOmax® is a gaseous blend of NO and nitrogen (0.08% and 99.92% respectively for 800 ppm; and 0.01% and 99.99% respectively for 100 ppm) and is supplied in aluminium cylinders as a compressed gas under high pressure. In general, INOmax® is administered to a patient in conjunction with ventilatory support and O$_2$. Delivery devices suitable for the safe and effective delivery of gaseous NO for inhalation include the INOvent®, INOmax DS®, INOpulse®, INOblender®, or other suitable drug delivery and regulation devices or components incorporated therein, or other related processes, which are described in various patent documents including U.S. Pat. Nos. 5,558,083; 5,732,693; 5,752,504; 5,732,694; 6,089,229; 6,109,260; 6,125,846; 6,164,276; 6,581,592; 5,918,596; 5,839,433; 7,114,510; 5,417,950; 5,670,125; 5,670,127; 5,692,495; 5,514,204; 7,523,752; 5,699,790; 5,885,621; U.S. patent application Ser. Nos. 11/355,670 (US 2007/0190184); 10/520,270 (US 2006/0093681); 11/401,722 (US 2007/0202083); 10/053,535 (US 2002/0155166); 10/367,277 (US 2003/0219496); 10/439,632 (US 2004/0052866); 10/371,666 (US 2003/0219497); 10/413,817 (US 2004/0005367); 12/050,826 (US 2008/0167609); and PCT/US2009/045266, all of which are incorporated herein by reference in their entirety.

Such devices deliver INOmax® into the inspiratory limb of the patient breathing circuit in a way that provides a constant concentration of NO to the patient throughout the inspired breath. Importantly, suitable delivery devices provide continuous integrated monitoring of inspired O$_2$, NO$_2$ and NO, a comprehensive alarm system, a suitable power source for uninterrupted NO delivery and a backup NO delivery capability.

As used herein, the term "children" (and variations thereof) includes those being around 4 weeks to 18 years of age.

As used herein, the term "adult" (and variations thereof) includes those being over 18 years of age.

As used herein, the terms "adverse event" or "AE" (and variations thereof) mean any untoward occurrence in a subject, or clinical investigation subject administered a pharmaceutical product (such as nitric oxide) and which does not necessarily have a causal relationship with such treatment. An adverse event can therefore be any unfavorable and unintended sign (including an abnormal laboratory finding), symptom, or disease temporarily associated with the use of a medicinal/investigational product, whether or not related to the investigational product. A relationship to the investigational product is not necessarily proven or implied. However, abnormal values are not reported as adverse events unless considered clinically significant by the investigator.

As used herein, the terms "adverse drug reaction" or "ADR" (and variations thereof) mean any noxious and unintended response to a medicinal product related to any dose.

As used herein, the terms "serious adverse event" or "SAE" (or "serious adverse drug reaction" or "serious ADR") (and variations thereof) mean a significant hazard or side effect, regardless of the investigator's opinion on the relationship to the investigational product. A serious adverse event or reaction is any untoward medical occurrence that at any dose: results in death; is life-threatening (which refers to an event/reaction where the patient was at risk of death at the time of the event/reaction, however this does not refer to an event/reaction that hypothetically may have caused death if it were more severe); requires inpatient hospitalization or results in prolongation of existing hospitalization; results in persistent or significant disability/incapacity; is a congenital anomaly/birth defect; or, is a medically important event or reaction. Medical and scientific judgment is exercised in deciding whether reporting is appropriate in other situations, such as important medical events that may not be immediately life threatening or result in death or hospitalization but may jeopardize the subject or may require medical or surgical intervention to prevent one of the other outcomes listed above—these are also considered serious. Examples of such medical events include cancer, allergic bronchospasm requiring intensive treatment in an emergency room or at home, blood dyscrasias or convulsions that do not result in hospitalizations, or the development of drug dependency or drug abuse. Serious clinical laboratory abnormalities directly associated with relevant clinical signs or symptoms are also reported.

Left Ventricular Dysfunction. Patients having pre-existing LVD may be described in general as those with elevated pulmonary capillary wedge pressure, including those with diastolic dysfunction (including hypertensive cardiomyopathy), those with systolic dysfunction, including those with cardiomyopathies (including ischemic or viral cardiomyopathy, or idiopathic cardiomyopathy, or autoimmune disease related cardiomyopathy, and side effects due to drug related or toxic-related cardiomyopathy), or structural heart disease, valvular heart disease, congenital heart disease, idiopathic pulmonary arterial hypertension, pulmonary hypertension and cardiomyopathy, or associations thereof. Identifying patients with pre-existing LVD is known to those skilled in the medicinal arts, and such techniques for example may include assessment of clinical signs and symptoms of heart failure, or echocardiography diagnostic screening.

Pulmonary Capillary Wedge Pressure. Pulmonary capillary wedge pressure, or "PCWP", provides an estimate of left atrial pressure. Identifying patients with pre-existing PCWP is known to those skilled in the medicinal arts, and such techniques for example may include measure by inserting balloon-tipped, multi-lumen catheter (also known as a Swan-Ganz catheter). Measure of PCWP may be used as a means to diagnose the severity of LVD (sometimes also referred to as left ventricular failure). PCWP is also a desired measure when evaluating pulmonary hypertension. Pulmonary hypertension is often caused by an increase in pulmonary vascular resistance (PVR), but may also arise from increases in pulmonary venous pressure and pulmonary blood volume secondary to left ventricular failure or mitral or aortic valve disease.

In cardiac physiology, afterload is used to mean the tension produced by a chamber of the heart in order to contract. If the chamber is not mentioned, it is usually assumed to be the left ventricle. However, the strict definition of the term relates to the properties of a single cardiac myocyte. It is therefore only of direct relevance in the laboratory; in the clinic, the term end-systolic pressure is usually more appropriate, although not equivalent.

The terms "left ventricular afterload" (and variations thereof) refer to the pressure that the chamber of the heart has to generate in order to eject blood out of the chamber. Thus, it is a consequence of the aortic pressure since the pressure in the ventricle must be greater than the systemic pressure in order to open the aortic valve. Everything else held equal, as afterload increases, cardiac output decreases. Disease processes that increase the left ventricular afterload include increased blood pressure and aortic valve disease. Hypertension (Increased blood pressure) increases the left ventricular afterload because the left ventricle has to work harder to eject blood into the aorta. This is because the aortic valve won't open until the pressure generated in the left ventricle is higher than the elevated blood pressure. Aortic stenosis increases the afterload because the left ventricle has to overcome the pressure gradient caused by the stenotic aortic valve in addition to the blood pressure in order to eject blood into the aorta. For instance, if the blood pressure is 120/80, and the aortic valve stenosis creates a trans-valvular gradient of 30 mmHg, the left ventricle has to generate a pressure of 110 mmHg in order to open the aortic valve and eject blood into the aorta. Aortic insufficiency increases afterload because a percentage of the blood that is ejected forward regurgitates back through the diseased aortic valve. This leads to elevated systolic blood pressure. The diastolic blood pressure would fall, due to regurgitation. This would result in an increase pulse pressure. Mitral regurgitation decreases the afterload. During ventricular systole, the blood can regurgitate through the diseased mitral valve as well as be ejected through the aortic valve. This means that the left ventricle has to work less to eject blood, causing a decreased afterload. Afterload is largely dependent upon aortic pressure.

An intra-aortic balloon pump (IABP) is a mechanical device that is used to decrease myocardial oxygen demand while at the same time increasing cardiac output. By increasing cardiac output it also increases coronary blood flow and therefore myocardial oxygen delivery. It consists of a cylindrical balloon that sits in the aorta and counterpulsates. That is, it actively deflates in systole increasing forward blood flow by reducing afterload thus, and actively inflates in diastole increasing blood flow to the coronary arteries. These actions have the combined result of decreasing myocardial oxygen demand and increasing myocardial oxygen supply. The balloon is inflated during diastole by a computer controlled mechanism, usually linked to either an ECG or a pressure transducer at the distal tip of the catheter; some IABPs, such as the Datascope System 98XT, allow for asynchronous counterpulsation at a set rate, though this setting is rarely used. The computer controls the flow of helium from a cylinder into and out of the balloon. Helium is used because its low viscosity allows it to travel quickly through the long connecting tubes, and has a lower risk of causing a harmful embolism should the balloon rupture while in use. Intraaortic balloon counterpulsation is used in situations when the heart's own cardiac output is insufficient to meet the oxygenation demands of the body. These situations could include cardiogenic shock, severe septic shock, post cardiac surgery and numerous other situations.

Patients eligible for treatment with iNO. In general, patients approved for treatment of iNO are term and near-term (>34 weeks gestation) neonates having hypoxic respiratory failure associated with clinical or echocardiographic evidence of pulmonary hypertension, a condition also known as persistent pulmonary hypertension in the newborn (PPHN). Due to the selective, non-systemic nature of iNO to reduce pulmonary hypertension, physicians skilled in the art further employ INOmax® to treat or prevent pulmonary hypertension and improve blood $O_2$ levels in a variety of other clinical settings, including in both pediatric and adult patients suffering from acute respiratory distress syndrome (ARDS), pediatric and adult patients undergoing cardiac or transplant surgeries, pediatric and adult patients for testing to diagnose reversible pulmonary hypertension, and in pediatric patients with congenital diaphragmatic hernia. In most, if not all, of these applications, INOmax® acts by preventing or treating reversible pulmonary vasoconstriction, reducing pulmonary arterial pressure and improving pulmonary gas exchange.

A small proportion of INOmax® sales stem from its use by clinicians in a premature infant population. In these patients, INOmax® is generally utilized by physicians as a rescue therapy primarily to vasodilate the lungs and improve pulmonary gas exchange. Some physicians speculate that INOmax® therapy may promote lung development and/or reduce or prevent the future development of lung disease in a subset of these patients. Although the precise mechanism(s) responsible for the benefits of INOmax® therapy in these patients is not completely understood, it appears that the benefits achieved in at least a majority of these patients are due to the ability of INOmax® to treat or prevent reversible pulmonary vasoconstriction.

In clinical practice, the use of INOmax® has reduced or eliminated the use of high risk systemic vasodilators for the treatment of PPHN. INOmax®, in contrast to systemic vasodilators, specifically dilates the pulmonary vasculature without dilating systemic blood vessels. Further, iNO preferentially vasodilates vessels of aveoli that are aerated, thus improving V/Q matching. In contrast, systemic vasodilators may increase blood flow to atelectatic (deflated or collapsed) alveoli, thereby increasing V/Q mismatch and worsening arterial oxygenation. (See Rubin L J, Kerr K M, Pulmonary Hypertension, in *Critical Care Medicine: Principles of Diagnosis and Management in the Adult*, 2d Ed., Parillo J E, Dellinger R P (eds.), Mosby, Inc. 2001, pp. 900-09 at 906;

Kinsella J P, Abman S H, The Role of Inhaled Nitric Oxide in Persistent Pulmonary Hypertension of the Newborn, in *Acute Respiratory Care of the Neonate: A Self-Study Course*, 2d Ed., Askin D F (ed.), NICU Ink Book Publishers, 1997, pp. 369-378 at 372-73).

INOmax® also possesses highly desirable pharmacokinetic properties as a lung-specific vasodilator when compared to other ostensibly "pulmonary-specific vasodilators." For example, the short half-life of INOmax® allows INOmax® to exhibit rapid "on" and "off" responses relative to INOmax® dosing, in contrast to non-gaseous alternatives. In this way, INOmax® can provide physicians with a useful therapeutic tool to easily control the magnitude and duration of the pulmonary vasodilatation desired. Also, the nearly instantaneous inactivation of INOmax® in the blood significantly reduces or prevents vasodilatation of non-pulmonary vessels.

The pivotal trials leading to the approval of INOmax® were the CINRGI and NINOS study.

CINRGI study. (See Davidson et al., March 1998, Inhaled Nitric Oxide for the Early Treatment of Persistent Pulmonary Hypertension of the term Newborn; A Randomized, Double-Masked, Placebo-Controlled, Dose-Response, Multicenter Study; *PEDIATRICS* Vol. 101, No. 3, p. 325).

This study was a double-blind, randomized, placebo-controlled, multicenter trial of 186 term and near-term neonates with pulmonary hypertension and hypoxic respiratory failure. The primary objective of the study was to determine whether INOmax® would reduce the receipt of extracorporeal membrane oxygenation (ECMO) in these patients. Hypoxic respiratory failure was caused by meconium aspiration syndrome (MAS) (35%), idiopathic persistent pulmonary hypertension of the newborn (PPHN) (30%), pneumonia/sepsis (24%), or respiratory distress syndrome (RDS) (8%). Patients with a mean $PaO_2$ of 54 mm Hg and a mean oxygenation index (OI) of 44 cm $H_2O$/mm Hg were randomly assigned to receive either 20 ppm INOmax® (n=97) or nitrogen gas (placebo; n=89) in addition to their ventilatory support. Patients that exhibited a $PaO_2$>60 mm Hg and a pH<7.55 were weaned to 5 ppm INOmax® or placebo. The primary results from the CINRGI study are presented in Table 4. ECMO was the primary endpoint of the study.

TABLE 1

Summary of Clinical Results from CINRGI Study

|  | Placebo | INOmax ® | P value |
|---|---|---|---|
| Death or ECMO | 51/89 (57%) | 30/97 (31%) | <0.001 |
| Death | 5/89 (6%) | 3/97 (3%) | 0.48 |

Significantly fewer neonates in the ECMO group required ECMO, and INOmax® significantly improved oxygenation, as measured by $PaO_2$, OI, and alveolar-arterial gradient.

NINOS study. (See Inhaled Nitric Oxide in Full-Term and Nearly Full-Term Infants with Hypoxic Respiratory Failure; NEJM, Vol. 336, No. 9, 597).

The Neonatal Inhaled Nitric Oxide Study (NINOS) group conducted a double-blind, randomized, placebo-controlled, multicenter trial in 235 neonates with hypoxic respiratory failure. The objective of the study was to determine whether iNO would reduce the occurrence of death and/or initiation of ECMO in a prospectively defined cohort of term or near-term neonates with hypoxic respiratory failure unresponsive to conventional therapy. Hypoxic respiratory failure was caused by meconium aspiration syndrome (MAS; 49%), pneumonia/sepsis (21%), idiopathic primary pulmonary hypertension of the newborn (PPHN; 17%), or respiratory distress syndrome (RDS; 11%). Infants≦14 days of age (mean, 1.7 days) with a mean $PaO_2$ of 46 mm Hg and a mean oxygenation index (OI) of 43 cm $H_2O$/mmHg were initially randomized to receive 100% $O_2$ with (n=114) or without (n=121) 20 ppm NO for up to 14 days. Response to study drug was defined as a change from baseline in $PaO_2$ 30 minutes after starting treatment (full response=>20 mmHg, partial=10-20 mm Hg, no response=<10 mm Hg). Neonates with a less than full response were evaluated for a response to 80 ppm NO or control gas. The primary results from the NINOS study are presented in Table 2.

TABLE 2

Summary of Clinical Results from NINOS Study

|  | Control (n = 121) | NO (n = 114) | P value |
|---|---|---|---|
| Death or ECMO *, † | 77 (64%) | 52 (46%) | 0.006 |
| Death | 20 (17%) | 16 (14%) | 0.60 |
| ECMO | 66 (55%) | 44 (39%) | 0.014 |

* Extracorporeal membrane oxygenation
† Death or need for ECMO was the study's primary end point Adverse Events from CINRGI & NINOS. Controlled studies have included 325 patients on INOmax® doses of 5 to 80 ppm and 251 patients on placebo. Total mortality in the pooled trials was 11% on placebo and 9% on INOmax®, a result adequate to exclude INOmax® mortality being more than 40% worse than placebo.

In both the NINOS and CINRGI studies, the duration of hospitalization was similar in INOmax® and placebo-treated groups.

From all controlled studies, at least 6 months of follow-up is available for 278 patients who received INOmax® and 212 patients who received placebo. Among these patients, there was no evidence of an AE of treatment on the need for re-hospitalization, special medical services, pulmonary disease, or neurological squeal.

In the NINOS study, treatment groups were similar with respect to the incidence and severity of intracranial hemorrhage, Grade IV hemorrhage, per ventricular leukomalacia, cerebral infarction, seizures requiring anticonvulsant therapy, pulmonary hemorrhage, or gastrointestinal hemorrhage.

The table below shows adverse reactions that occurred in at least 5% of patients receiving INOmax® in the CINRGI study. None of the differences in these adverse reactions were statistically significant when iNO patients were compared to patients receiving placebo.

TABLE 3

ADVERSE REACTIONS ON THE CINRGI TRIAL

| Adverse Reaction | Placebo (n = 89) | Inhaled NO (n = 97) |
|---|---|---|
| Atelectasis | 5 (4.8%) | 7 (6.5%) |
| Bilirubinemia | 6 (5.8%) | 7 (6.5%) |
| Hypokalemia | 5 (4.8%) | 9 (8.3%) |
| Hypotension | 3 (2.9%) | 6 (5.6%) |
| Thrombocytopenia | 20 (19.2%) | 16 (14.8%) |

Post-Marketing Experience. The following AEs have been reported as part of the post-marketing surveillance. These events have not been reported above. Given the nature of spontaneously reported post-marketing surveillance data, it is impossible to determine the actual incidence of the events or definitively establish their causal relationship to the drug. The listing is alphabetical: dose errors associated with the delivery system; headaches associated with environmental exposure of INOmax® in hospital staff; hypotension associated with acute withdrawal of the drug; hypoxemia associated with acute withdrawal of the drug; pulmonary edema in patients with CREST syndrome.

An analysis of AEs and SAEs from both the CINRGI and NINOS studies, in addition to post-marketing surveillance, did not suggest that patients who have pre-existing LVD could experience an increased risk of AEs or SAEs. Nor was it predictable to physicians skilled in the art that patients having pre-existing LVD (possibly identified as those patients having a PCWP greater than 20 mmHg) should be evaluated in view of the benefit versus risk of using iNO in patients with clinically significant LVD, and that these patients should be evaluated on a case by case basis.

Example 1

INOT22 Study

The INOT22, entitled "Comparison of supplemental oxygen and nitric oxide for inhalation plus oxygen in the evaluation of the reactivity of the pulmonary vasculature during acute pulmonary vasodilatory testing" was conducted both to access the safety and effectiveness of INOmax® as a diagnostic agent in patients undergoing assessment of pulmonary hypertension (primary endpoint), and to confirm the hypothesis that iNO is selective for the pulmonary vasculature (secondary endpoint).

During, and upon final analysis of the INOT22 study results, applicants discovered that rapidly decreasing the pulmonary vascular resistance, via the administration of iNO to a patient in need of such treatment, may be detrimental to patients with concomitant, pre-existing LVD. Therefore, a precaution for patients with LVD was proposed to be included in amended prescribing information for INOmax®. Physicians were further informed to consider reducing left ventricular afterload to minimize the occurrence of pulmonary edema in patients with pre-existing LVD.

In particular, the INOT22 protocol studied consecutive children undergoing cardiac catheterization that were prospectively enrolled at 16 centers in the US and Europe. Inclusion criteria: 4 weeks to 18 years of age, pulmonary hypertension diagnosis, i.e. either idiopathic pulmonary hypertension (IPAH) or related to congenital heart disease (CHD) (repaired or unrepaired) or cardiomyopathy, with pulmonary vascular resistance index (PVRI)>3 u-m$^2$. Later amendments, as discussed herein, added an additional inclusionary criteria of a PCWP less than 20 gmm Hg. Patients were studied under general anaesthesia, or with conscious sedation, according to the practice of the investigator. Exclusion criteria: focal infiltrates on chest X-ray, history of intrinsic lung disease, and/or currently taking PDE-5 inhibitors, prostacyclin analogues or sodium nitroprusside. The study involved supplemental $O_2$ and NO for inhalation plus $O_2$ in the evaluation of the reactivity of the pulmonary vasculature during acute pulmonary vasodilator testing. Consecutive children undergoing cardiac catheterization were prospectively enrolled at 16 centers in the US and Europe. As hypotension is expected in these neonatal populations, the comparison between iNO and placebo groups is difficult to assess. A specific secondary endpoint was evaluated in study INOT22 to provide a more definitive evaluation.

The primary objective was to compare the response frequency with iNO and $O_2$ vs. $O_2$ alone; in addition, all subjects were studied with iNO alone. Patients were studied during five periods: Baseline 1, Treatment Period 1, Treatment Period 2, Baseline 2 and Treatment Period 3. All patients received all three treatments; treatment sequence was randomized by center in blocks of 4; in Period 1, patients received either NO alone or $O_2$ alone, and the alternate treatment in Period 3. All patients received the iNO and $O_2$ combination treatment in Period 2. Once the sequence was assigned, treatment was unblinded. Each treatment was given for 10 minutes prior to obtaining hemodynamic measurements, and the Baseline Period 2 was at least 10 minutes.

Results for the intent-to-treat (ITT) population, defined as all patients who were randomized to receive drug, indicated that treatment with NO plus $O_2$ and $O_2$ alone significantly increased systemic vascular resistance index (SVRI) (Table 4). The change from baseline for NO plus $O_2$ was 1.4 Woods Units per meter$^2$ (WU·m$^2$) (p=0.007) and that for $O_2$ was 1.3 WU·m$^2$ (p=0.004). While the change from baseline in SVRI with NO alone was −0.2 WU·m$^2$ (p=0.899) which demonstrates a lack of systemic effect.

TABLE 4

SVRI Change From Baseline by Treatment (Intent-to-Treat)

| | Treatment | | |
|---|---|---|---|
| SVRI (WU · m$^2$) | NO Plus $O_2$ (n = 109) | $O_2$ (n = 106) | NO (n = 106) |
| Baseline (room air) | | | |
| Mean | 17.2 | 17.6 | 18.0 |
| Standard Deviation (SD) | 8.86 | 9.22 | 8.44 |
| Median | 15.9 | 16.1 | 16.2 |
| Minimum, maximum | −7.6, 55.6 | −7.6, 55.6 | 1.9, 44.8 |
| Post-treatment | | | |
| Mean | 18.7 | 18.9 | 17.8 |
| SD | 9.04 | 8.78 | 9.40 |
| Median | 17.1 | 17.1 | 15.4 |
| Minimum, maximum | 3.0, 47.4 | 3.9, 43.6 | 3.3, 50.7 |
| Change From Baseline | | | |
| Mean | 1.4 | 1.3 | −0.2 |
| SD | 5.94 | 5.16 | 4.65 |
| Median | 1.2 | 1.0 | 0.2 |
| Minimum, maximum | −20.5, 19.1 | −18.1, 17.7 | −12.5, 12.7 |
| p-value$^a$ | 0.007 | 0.004 | 0.899 |

Pairwise comparisons
NO plus $O_2$ versus $O_2$, p = 0.952
NO plus $O_2$ versus NO, p = 0.014
$O_2$ versus NO, p = 0.017
$^a$p-value from a Wilcoxon Signed Rank Test. Only patients with data to determine response at both treatments are included in this analysis.
Source: INOT22 CSR Table 6.4.1 and Appendix 16.2.6 (ATTACHMENT 1)

The ideal pulmonary vasodilator should reduce PVRI and/or PAPm while having no appreciable effect on systemic blood pressure or SVRI. In this case, the ratio of PVRI to SVRI would decrease, given some measure of the selectivity of the agent for the pulmonary vascular bed. The change in the ratio of PVRI to SVRI by treatment is shown in Table 5.

TABLE 5

Change in Ratio of PVRI to SVRI by Treatment (Intent-to-Treat)

| | Treatment | | |
|---|---|---|---|
| Ratio PVRI/SVRI | NO Plus $O_2$ (n = 108) | $O_2$ (n = 105) | NO (n = 106) |
| Baseline | | | |
| Mean | 0.6 | 0.5 | 0.6 |
| SD | 0.60 | 0.45 | 0.56 |

TABLE 5-continued

Change in Ratio of PVRI to SVRI by Treatment (Intent-to-Treat)

| Ratio PVRI/SVRI | Treatment | | |
|---|---|---|---|
| | NO Plus $O_2$ (n = 108) | $O_2$ (n = 105) | NO (n = 106) |
| Median | 0.5 | 0.5 | 0.4 |
| Minimum, Maximum | −1.6, 4.7 | −1.6, 1.8 | 0.0, 4.7 |
| Post Treatment | | | |
| Mean | 0.4 | 0.4 | 0.5 |
| SD | 0.31 | 0.31 | 0.46 |
| Median | 0.3 | 0.4 | 0.3 |
| Minimum, Maximum | 0.0, 1.3 | 0.0, 1.4 | −1.2, 2.2 |
| Change from Baseline | | | |
| Mean | −0.2 | −0.1 | −0.1 |
| SD | 0.52 | 0.31 | 0.54 |
| Median | −0.1 | −0.1 | 0.0 |
| Minimum, Maximum | −4.4, 2.0 | −1.6, 2.0 | −4.4, 1.6 |
| P Value[1] | <0.001 | <0.001 | 0.002 |

[1]Wilcoxon Signed Rank Test
Source: INOT22 CSR Table 6.5.1 (ATTACHMENT 2)

All three treatments have a preferential effect on the pulmonary vascular bed, suggesting that all three are selective pulmonary vasodilators. The greatest reduction in the ratio was during treatment with NO plus $O_2$, possibly due to the decrease in SVRI effects seen with $O_2$ and NO plus $O_2$. These results are displayed as percent change in the ratio (See Table 6).

TABLE 6

Percent Change in Ratio of PVRI to SVRI by Treatment (Intent-to-Treat)

| Ratio PVRI/SVRI | Treatment | | |
|---|---|---|---|
| | NO Plus $O_2$ (n = 108) | $O_2$ (n = 105) | NO (n = 106) |
| Baseline | | | |
| Mean | 0.6 | 0.5 | 0.6 |
| SD | 0.60 | 0.45 | 0.56 |
| Median | 0.5 | 0.5 | 0.4 |
| Minimum, Maximum | −1.6, 4.7 | −1.6, 1.8 | 0.0, 4.7 |
| Post Treatment | | | |
| Mean | 0.4 | 0.4 | 0.5 |
| SD | 0.31 | 0.31 | 0.46 |
| Median | 0.3 | 0.4 | 0.3 |
| Minimum, Maximum | 0.0, 1.3 | 0.0, 1.4 | −1.2, 2.2 |
| Percent Change from Baseline | | | |
| Mean | −33.5 | −19.3 | −6.2 |
| SD | 36.11 | 34.59 | 64.04 |
| Median | −34.0 | −21.3 | −13.8 |
| Minimum, Maximum | −122.2, 140.1 | −122.7, 93.3 | −256.1, 294.1 |
| P Value[1] | <0.001 | <0.001 | 0.006 |

[1]Wilcoxon Signed Rank Test
Source: INOT22 CSR Table 6.5.2 (ATTACHMENT 3)

NO plus $O_2$ appeared to provide the greatest reduction in the ratio, suggesting that NO plus $O_2$ was more selective for the pulmonary vasculature than either agent alone.

Overview of Cardiovascular Safety. In the INOT22 diagnostic study, all treatments (NO plus $O_2$, $O_2$, and NO) were well-tolerated. Seven patients of 134 treated experienced an AE during the study. These included cardiac arrest, bradycardia, low cardiac output (CO) syndrome, elevated ST segment (the portion of an electrocardiogram between the end of the QRS complex and the beginning of the T wave) on the electrocardiography (ECG) decreased $O_2$ saturation, hypotension, mouth hemorrhage and pulmonary hypertension (PH). The numbers of patients and events were too small to determine whether risk for AEs differed by treatment, diagnosis, age, gender or race. Eight patients are shown in Table 5 due to the time period in which events are reported. AEs were reported for 12 hours or until hospital discharge (which limits the period in which such events can be reported). There is technically no time limit in which SAEs are to be reported. So, there were 7 AEs during the study and at least one SAE after the study.

A total of 4 patients had AEs assessed as being related to study drug. These events included bradycardia, low CO syndrome, ST segment elevation on the ECG, low $O_2$ saturation, PH and hypotension. All but 2 AEs were mild or moderate in intensity and were resolved. Study treatments had slight and non-clinically significant effects on vital signs including heart rate, systolic arterial pressure and diastolic arterial pressure. When an investigator records an AE, they are required to say if (in their opinion) the event is related to the treatment or not. In this case, 4 of 7 were considered by the investigator to be related to treatment.

The upper limit of normal PCWP in children is 10-12 mm Hg and 15 mm Hg in adults. In INOT22, a baseline PCWP value was not included as exclusion criteria. However, after the surprising and unexpected identification of SAEs in the early tested patients, it was determined that patients with pre-existing LVD had an increased risk of experiencing an AE or SAE upon administration (e.g., worsening of left ventricular function due to the increased flow of blood through the lungs). Accordingly, the protocol for INOT22 was thereafter amended to exclude patients with a baseline PCWP greater than 20 mm Hg after one patient experienced acute circulatory collapse and died during the study. The value "20 mm Hg" was selected to avoid enrollment of a pediatric population with LVD such that they would be most likely at-risk for these SAEs.

SAEs were collected from the start of study treatment until hospital discharge or 12 hours, whichever occurred sooner. Three SAEs were reported during the study period, and a total of 7 SAEs were reported. Three of these were fatal SAEs and 4 were nonfatal (one of which led to study discontinuation). In addition, one non-serious AE also lead to discontinuation. A list of subjects who died, discontinued or experienced an SAE is provided in Table 5 below.

TABLE 5

Subjects that died, discontinued or experienced SAEs

| Patient number | AE | Serious? | Fatal? | Discontinued treatment? |
|---|---|---|---|---|
| 01020 | Desaturation (hypoxia) | No | No | Yes |
| 02002 | Pulmonary edema | Yes | No | No |
| 04001 | Hypotension and cardiac arrest | Yes | Yes | No |
| 04003 | Hypotension and ECG changes | Yes | No | Yes |
| 04008 | Hypotension and hypoxemia | Yes | Yes | No |
| 05002 | Hypoxia and bradycardia (also pulmonary edema) | Yes | Yes | No |
| 07003 | Cardiac arrest | Yes | No | No |
| 17001 | Hypoxia | Yes | No | No |

Two of the 3 fatal SAEs were deemed related to therapy. All 4 non-fatal SAEs were also considered related to therapy. The numbers of patients and events were too small to determine whether risk for SAEs differed by treatment, diagnosis, age, gender or race. At least two patients developed signs of pulmonary edema (subjects 05002 and 02002). This is of interest because pulmonary edema has previously been reported with the use of iNO in patients with LVD, and may be related to decreasing PVRI and overfilling of the left atrium. (Hayward C S et al., 1996, Inhaled Nitric Oxide in Cardiac Failure: Vascular Versus Ventricular Effects, *J Cardiovascular Pharmacology* 27:80-85; Bocchi E A et al., 1994, Inhaled Nitric Oxide Leading to Pulmonary Edema in Stable Severe Heart Failure, *Am J Cardiology* 74:70-72; and, Semigran M J et al., 1994, Hemodynamic Effects of Inhaled Nitric Oxide in Heart Failure, *J Am Coll Cardiology* 24:982-988).

Although the SAE rate is within range for this population, it appears that patients with the most elevated PCWP at baseline had a disproportionately high number of these events. (Bocchi E A et al., 1994; Semigran M J et al., 1994).

In the INOT22 study, 10 of the total 134 patients had a baseline PCWP≧18 mm Hg (7.5%), of which, 3 subjects (04001, 02002 and 04003) had a SAE or were prematurely discontinued from the study (30%) compared to 6.5% for the entire cohort.

Although there were very few significant AEs in the INOT22 study, these events are consistent with the expected physiologic changes in patients with severe LVD. The events also corroborate prior observations that iNO is rapidly acting, selective for the pulmonary vasculature, and well-tolerated in most patients. The actual incidence of acute LVD during acute ventricular failure (AVT) is unknown. However, it is reasonable to expect that a significant number of patients are at-risk for an increased incidence of SAEs upon iNO treatment based upon the nature of the underlying nature of the illness, i.e., pulmonary hypertension and cardiovascular disease more generally. Thus, it would be advantageous to have physicians identify these patients prior to beginning iNO treatment, so that the physicians are alerted to this possible outcome.

Benefits and Risks Conclusions. The INOT22 study was designed to demonstrate the physiologic effects of iNO in a well defined cohort of children (i.e., intended patient population) with pulmonary hypertension using a high concentration, 80 ppm, of iNO, i.e., one that would be expected to have the maximal pharmacodynamic effect. INOT22 was the largest and most rigorous pharmacodynamic study of iNO conducted to date, and it confirms a number of prior observations, such as iNO being rapidly acting, selective for the pulmonary vasculature, and well-tolerated in most patients.

It is also acknowledged that rapidly decreasing the PVR may be undesirable and even dangerous in patients with concomitant LVD. In the INOT22 study, the overall numbers of SAEs and fatal SAEs are within the expected range for patients with this degree of cardiopulmonary disease. The overall rate is 7/124 (5.6%), which is closely comparable to the rate of 6% recently reported in a very similar cohort of patients. (Taylor C J et al., 2007, Risk of cardiac catheterization under anaesthesia in children with pulmonary hypertension, *Br J Anaesth* 98(5):657-61). Thus, the overall rate of SAEs would seem to be more closely related to the underlying severity of illness of the patients rather than to the treatments given during this study.

The INOT22 study results demonstrate that patients who had pre-existing LVD may experience an increased rate of SAEs (e.g., pulmonary edema). During the course of the study, the protocol was amended to exclude patients with a PCWP>20 mmHg. The benefit/risk of using iNO in patients with clinically significant LVD should be evaluated on a case by case basis. A reduction in left ventricular afterload may perhaps be applied to minimize the occurrence of pulmonary edema.

We claim:

1. A method of reducing the risk of occurrence of pulmonary edema associated with a medical treatment comprising inhalation of 20 ppm nitric oxide gas, said method comprising:
    (a) performing echocardiography to identify a child in need of 20 ppm inhaled nitric oxide treatment for pulmonary hypertension, wherein the child is not dependent on right-to-left shunting of blood;
    (b) determining that the child identified in (a) has a pulmonary capillary wedge pressure greater than or equal to 20 mm Hg and thus has left ventricular dysfunction, so is at particular risk of pulmonary edema upon treatment with inhaled nitric oxide; and
    (c) excluding the child from inhaled nitric oxide treatment based on the determination that the child has left ventricular dysfunction and so is at particular risk of pulmonary edema upon treatment with inhaled nitric oxide.

2. The method of claim 1, wherein the child is a neonate.

3. The method of claim 1, wherein step (b) comprises measuring the child's pulmonary capillary wedge pressure.

4. The method of claim 1, wherein the child's left ventricular dysfunction is attributable to congenital heart disease.

5. The method of claim 1, wherein the child is determined to be at particular risk not only of pulmonary edema, but also of other Serious Adverse Events, upon treatment with inhaled nitric oxide, and the child is excluded from inhaled nitric oxide treatment based on the determination that the child has left ventricular dysfunction and so is at particular risk not only of pulmonary edema, but also of other Serious Adverse Events, upon treatment with inhaled nitric oxide.

6. A method of reducing the risk of occurrence of pulmonary edema associated with a medical treatment comprising inhalation of 20 ppm nitric oxide gas, said method comprising:
    (a) carrying out a diagnostic process comprising measuring blood oxygen level, to identify a child as being in need of 20 ppm inhaled nitric oxide treatment for hypoxic respiratory failure, wherein the child is not dependent on right-to-left shunting of blood;
    (b) determine determining that the child has a pulmonary capillary wedge pressure greater than or equal to 20 mm Hg and thus has left ventricular dysfunction, so is at particular risk of pulmonary edema upon treatment with inhaled nitric oxide; and
    (c) excluding the child from treatment with inhaled nitric oxide based on the determination that the child has left ventricular dysfunction and so is at particular risk of pulmonary edema upon treatment with inhaled nitric oxide.

7. The method of claim 6, wherein the diagnostic process of step (a) further comprises performing echocardiography.

8. The method of claim 6, wherein the child is a neonate.

9. The method of claim 6, wherein step (b) comprises measuring the child's pulmonary capillary wedge pressure.

10. The method of claim 6, wherein the left ventricular dysfunction is attributable to congenital heart disease.

11. The method of claim 6, wherein the child is determined to be at particular risk not only of pulmonary edema, but also of other Serious Adverse Events, upon treatment with inhaled nitric oxide, and the child is excluded from inhaled nitric oxide treatment based on the determination that the child has left ventricular dysfunction and so is at particular risk not only of pulmonary edema, but also other Serious Adverse Events, upon treatment with inhaled nitric oxide.

12. The method of claim 11, wherein the left ventricular dysfunction is attributable to congenital heart disease.

13. A method of treatment comprising:
(a) performing echocardiography to identify a plurality of children who are in need of 20 ppm inhaled nitric oxide treatment for pulmonary hypertension, wherein the children are not dependent on right-to-left shunting of blood;
(b) determining that a first child of the plurality has a pulmonary capillary wedge pressure greater than or equal to 20 mm Hg and thus has left ventricular dysfunction, so is at particular risk of pulmonary edema upon treatment with inhaled nitric oxide;
(c) determining that a second child of the plurality does not have left ventricular dysfunction;
(d) administering the 20 ppm inhaled nitric oxide treatment to the second child; and
(e) excluding the first child from treatment with inhaled nitric oxide, based on the determination that the first child has left ventricular dysfunction, so is at particular risk of pulmonary edema upon treatment with inhaled nitric oxide.

14. The method of claim 13, wherein step (a) further comprises measuring blood oxygen levels in the first and second children and thereby determining that the first and second children are hypoxic.

15. The method of claim 13, wherein the second child has congenital heart disease.

16. The method of claim 13, wherein step (b) comprises measuring the first child's pulmonary capillary wedge pressure.

17. The method of claim 13, wherein determining that the second child of the plurality does not have pre-existing left ventricular dysfunction comprises performing echocardiography.

18. The method of claim 13, wherein the left ventricular dysfunction is attributable to congenital heart disease.

19. The method of claim 13, wherein the left ventricular dysfunction of the first child is attributable to congenital heart disease.

20. The method of claim 13, wherein the first child is determined to be at particular risk not only of pulmonary edema, but also of other Serious Adverse Events, upon treatment with inhaled nitric oxide, and the first child is excluded from inhaled nitric oxide treatment based on the determination that the first child has left ventricular dysfunction and so is at particular risk not only of pulmonary edema, but also other Serious Adverse Events, upon treatment with inhaled nitric oxide.

21. The method of claim 20, wherein the pre-existing left ventricular dysfunction of the first child is attributable to congenital heart disease.

22. A method of treatment comprising:
(a) identifying a plurality of children who are in need of 20 ppm inhaled nitric oxide treatment, wherein the children are not dependent on right-to-left shunting of blood;
(b) in the first child of the plurality, measuring pulmonary capillary wedge pressure to determine that the first child of the plurality has a pulmonary capillary wedge pressure greater than or equal to 20 mm Hg and thus has left ventricular dysfunction, so is at particular risk of pulmonary edema upon treatment with inhaled nitric oxide;
(c) in the second child of the plurality, performing echocardiography and/or measurement of pulmonary capillary wedge pressure to determine that the second child of the plurality does not have left ventricular dysfunction;
(d) administering the 20 ppm inhaled nitric oxide treatment to the second child; and
(e) excluding the first child from treatment with inhaled nitric oxide, based on the determination that the first child has left ventricular dysfunction, so is at particular risk of pulmonary edema upon treatment with inhaled nitric oxide.

23. The method of claim 22, wherein step (a) comprises performing echocardiography to determine that the first and second children have pulmonary hypertension.

24. The method of claim 22, wherein step (a) comprises measuring blood oxygen levels in the first and second children and thereby determining that the first and second children are hypoxic.

25. The method of claim 22, wherein the second child has congenital heart disease.

26. The method of claim 22, wherein the left ventricular dysfunction is attributable to congenital heart disease.

27. The method of claim 22, wherein the pre-existing left ventricular dysfunction of the first child is attributable to congenital heart disease.

28. The method of claim 22, wherein the first child is determined to be at particular risk not only of pulmonary edema, but also of other Serious Adverse Events, upon treatment with inhaled nitric oxide, and the first child is excluded from inhaled nitric oxide treatment based on the determination that the first child has pre-existing left ventricular dysfunction and so is at particular risk not only of pulmonary edema, but also other Serious Adverse Events, upon treatment with inhaled nitric oxide.

29. The method of claim 28, wherein the pre-existing left ventricular dysfunction of the first child is attributable to congenital heart disease.

* * * * *

UNITED STATES PATENT AND TRADEMARK OFFICE
CERTIFICATE OF CORRECTION

| | |
|---|---|
| PATENT NO. | : 8,282,966 B2 |
| APPLICATION NO. | : 12/821020 |
| DATED | : October 9, 2012 |
| INVENTOR(S) | : James S. Baldassarre |

It is certified that error appears in the above-identified patent and that said Letters Patent is hereby corrected as shown below:

Title Page 1, Column 2, item [56] (OTHER PUBLICATIONS), line 6:

After "638)" insert -- . --.

Title Page 1, Column 2, item [56] (OTHER PUBLICATIONS), lines 8-9:

Delete "Bocchi the American Journal of Cardiology 1994, 74, pp.70-72. 4 pages)." and insert therefor -- Bocchi et al., (The American Journal of Cardiology 1994, 74, pp. 70-72). 4 pages. --.

Title Page 1, Column 2, item [56] (OTHER PUBLICATIONS), line 14:

Delete "(Achives" and insert -- (Archives -- therefor.

Title Page 1, Column 2, item [56] (OTHER PUBLICATIONS), line 14:

Delete "F47-F49." and insert -- F47-F49). -- therefor.

Title Page 1, Column 2, item [56] (OTHER PUBLICATIONS), lines 24-25:

Delete "Bocchi et al. The American Journal of Cardiology 1994, 74, pp:70-72. 4 pages).".

Title Page 1, Column 2, item [56] (OTHER PUBLICATIONS), line 36:

Delete "Adatia et al," and insert -- Adatia et al., -- therefor.

Title Page 1, right column, item [56] (OTHER PUBLICATIONS), line 37:

Delete "Hyptertension" and insert -- Hypertension -- therefor.

Signed and Sealed this
Sixteenth Day of April, 2013

Teresa Stanek Rea
*Acting Director of the United States Patent and Trademark Office*

CERTIFICATE OF CORRECTION (continued)
U.S. Pat. No. 8,282,966 B2

<u>Title Page 1, right column, item [56] (OTHER PUBLICATIONS), lines 42-45:</u>

Delete "Argenziano, et al., "Inhaled Nitric Oxide is not a Myocardial Depressant in a Porcine Model of Heart Failure", The Journal of Thoracic and Cardiovascular Surgery, 1998, vol. 115, pp. 700-704." and insert the same as a new entry beginning at page 1, right column, line 43.

<u>Title Page 1, right column, item [56] (OTHER PUBLICATIONS), line 55:</u>

Delete "Hypertemsion:" and insert -- Hypertension -- therefor.

<u>Title Page 1, right column, item [56] (OTHER PUBLICATIONS), line 59:</u>

Delete "dysfuction" and insert -- dysfunction -- therefor.

In the Specifications:

<u>Column 12, line 6:</u>

Delete "Table 5" and insert -- Table 7 -- therefor.

<u>Column 12, line 46:</u>

Delete "Table 5" and insert -- Table 7 -- therefor.

<u>Column 12, line 48:</u>

Delete the table heading "TABLE 5" and insert -- TABLE 7 -- therefor.

In the Claims:

<u>Column 14, Claim 6, line 45:</u>

Delete "determine".

UNITED STATES PATENT AND TRADEMARK OFFICE
CERTIFICATE OF CORRECTION

PATENT NO. : 8,282,966 B2
APPLICATION NO. : 12/821020
DATED : October 9, 2012
INVENTOR(S) : James S. Baldassarre It is certified that error appears in the above-identified patent and that said Letters Patent is hereby corrected as shown below:

In the Specifications:

Column 12, line 46:

Delete "Table 5" and insert -- Table 7 -- therefor.

Signed and Sealed this
Thirtieth Day of April, 2013

Teresa Stanek Rea
*Acting Director of the United States Patent and Trademark Office*